United States Patent
Waller et al.

(10) Patent No.: US 10,117,779 B2
(45) Date of Patent: Nov. 6, 2018

(54) GOGGLES

(75) Inventors: Tom Waller, Nottingham (GB); Chris Johnson, Nottingham (GB); Joseph Santry, Nottingham (GB)

(73) Assignee: SPEEDO INTERNATIONAL LIMITED, London (GB)

(*) Notice: Subject to any disclaimer, the term of this patent is extended or adjusted under 35 U.S.C. 154(b) by 355 days.

(21) Appl. No.: 14/123,697

(22) PCT Filed: Jun. 1, 2012

(86) PCT No.: PCT/GB2012/051239
§ 371 (c)(1),
(2), (4) Date: Dec. 3, 2013

(87) PCT Pub. No.: WO2012/164297
PCT Pub. Date: Dec. 6, 2012

(65) Prior Publication Data
US 2014/0115760 A1    May 1, 2014

(30) Foreign Application Priority Data

Jun. 3, 2011   (GB) .................................. 1109408.3
Jun. 3, 2011   (GB) .................................. 1109411.7
(Continued)

(51) Int. Cl.
*A61F 9/02*   (2006.01)
*A63B 33/00*  (2006.01)

(52) U.S. Cl.
CPC .............. *A61F 9/029* (2013.01); *A61F 9/027* (2013.01); *A63B 33/002* (2013.01); *A63B 2033/004* (2013.01)

(58) Field of Classification Search
CPC . A61F 9/02; A61F 9/027; A61F 9/029; A63B 33/002; A63B 2033/004
(Continued)

(56) References Cited

U.S. PATENT DOCUMENTS 2,568,316 A    9/1951  Brown
4,520,510 A *  6/1985  Daigle ................... A61F 9/029
                                                      2/12
(Continued)

FOREIGN PATENT DOCUMENTS

CN    1626259    6/2005
DE    685 459    12/1939
(Continued)

OTHER PUBLICATIONS

International Search Report for PCT/GB2012/051239 dated Jul. 13, 2012.
(Continued)

*Primary Examiner* — Richale Quinn
*Assistant Examiner* — Anne Kozak
(74) *Attorney, Agent, or Firm* — Marvin Petry; Stites & Harbison, PLLC

(57) ABSTRACT

The present invention relates to goggles, preferably extra-orbital goggles, having an outer surface defined by a pair of lens portions each having an upper and a lower peripheral wall. The upper and lower peripheral walls extend to an upper and lower peripheral edge respectively which, in use, are in contact with the wearers face. The outer surface defined by the upper peripheral walls is convex. This contributes to a goggle outer surface which is a smooth curve.

9 Claims, 10 Drawing Sheets

(30) Foreign Application Priority Data

Oct. 21, 2011 (GB) .................................. 1118280.5
Nov. 24, 2011 (GB) .................................. 1120358.5

(58) Field of Classification Search
USPC .................................. 2/426, 428, 439, 431
See application file for complete search history.

(56) References Cited

U.S. PATENT DOCUMENTS

| | | | |
|---|---|---|---|
| 5,313,671 A | | 5/1994 | Flory |
| 5,425,380 A | * | 6/1995 | Hudson .................. A61F 9/026 128/858 |
| 5,555,571 A | * | 9/1996 | McCaffrey .............. B63C 11/12 2/428 |
| 5,713,078 A | | 2/1998 | De Angelis |
| 6,098,206 A | * | 8/2000 | Chou .................. A63B 33/002 2/428 |
| 6,473,909 B1 | * | 11/2002 | Chou ...................... A61F 9/026 2/428 |
| 6,499,148 B2 | * | 12/2002 | Chou ..................... A63B 33/00 2/428 |
| 8,272,071 B2 | * | 9/2012 | Kaiser ....................... A61F 9/04 2/15 |
| D675,243 S | * | 1/2013 | Waller .......................... D16/311 |
| D695,334 S | * | 12/2013 | Waller .......................... D16/311 |
| 2002/0157174 A1 | | 10/2002 | Chou |
| 2005/0125883 A1 | | 6/2005 | Fukasawa |
| 2005/0273913 A1 | | 12/2005 | Chiang |
| 2007/0017007 A1 | * | 1/2007 | McBride .............. A63B 33/002 2/426 |
| 2008/0010728 A1 | | 1/2008 | Speed |
| 2009/0276941 A1 | | 11/2009 | Keegan |

FOREIGN PATENT DOCUMENTS

| | | |
|---|---|---|
| DE | 299 13 342 | 12/1999 |
| EP | 1 153 630 | 11/2001 |
| GB | 2 326 078 | 12/1998 |
| GB | 2 410 806 | 8/2005 |
| GB | 2 447 866 | 10/2008 |
| GB | 2482760 | 2/2012 |
| JP | 09-140829 | 6/1997 |
| WO | WO 98/57605 | 12/1998 |

OTHER PUBLICATIONS

Written Opinion by They International Searching Authority for PCT/GB2012/051239 dated Jul. 13, 2012.
Fourth Office Action for Chinese Application No. 201280032032.9, dated Dec. 30, 2016, The State Intellectual Property Office of People's Republic of China, Beijing, CN.
Notificiation of Reasons for Refusal for Japanese Application No. 2014-513247, dated Jan. 17, 2017, Japanese Patent Office, Tokyo, JP.
Combined Search and Examination Report Under Sections 17 and 18(3) for Application No. GB1120358.5, Claims Searched 1-11, 63 and 64, dated Jan. 20, 2012, Intellectual Property Office, UK.
Further Search Report Under Section 17 for Application No. GB1120358.5, Claims Searched 21-31, 52 and 63-65, dated Apr. 10, 2012, Intellectual Property Office, UK.
Further Search Report Under Section 17 for Application No. GB1120358.5, Claims Searched 43-52 and 63-65, Apr. 10, 2012, Intellectual Property Office, UK.
Russian Decision on Grant of a Patent for Invention, Application No. 2013157918/14(090214), Application filing date: Jun. 1, 2012, 12 pages.

* cited by examiner

GOGGLES

FIELD OF THE INVENTION

The present invention relates to goggles. In particular the present application relates to goggles for streamlining the wearer's head in order to reduce drag/resistance as the wearer moves.

BACKGROUND

It is often desirable for a wearer to wear goggles to protect the wearer's eyes and/or improve vision. For example, a swimmer may wear goggles to prevent water from contacting the wearer's eyes as this can cause discomfort and impairment to the wearer's vision.

Swimming goggles typically have a pair of front lens portions surrounded by a respective wall which extends back to and forms a seal with the wearer's face. The seals minimise contact between the wearer's eyes and the water.

Competitive swimmers are keen to minimise drag/water resistance as they move through the water in order to increase their speed. Known goggles can increase drag/water resistance as they protrude from the wearer's face and the walls can create a surface against which water can impact thus creating drag/water resistance. The impact of the water against the walls can also dislodge the goggles thus compromising the seal against the wearer's face and allowing the undesirable ingress of water into the goggles.

It is the aim of the present invention to provide goggles which minimise drag/water resistance as the wearer moves through water and minimise the possibility of dislodgement of the goggles (even in the absence of a head strap) which thus minimises the ingress of water.

SUMMARY OF THE INVENTION

In a first aspect, the present invention provides goggles having an outer surface defined by a pair of lens portions each having an upper and a lower peripheral wall extending to an upper and lower peripheral edge respectively wherein, in use, said peripheral edges are in contact with the wearer's face, and wherein the outer surface (i.e. the surface which faces away from the wearer and which, in use, is in contact with water) defined by the upper peripheral walls is convex.

Many known goggles have a substantially planar upper peripheral wall and this, necessarily extends back from the lens portion at substantially 90 degrees to the lens portion. This presents a prominent leading edge which creates considerable water resistance. By providing an upper peripheral wall having a convex outer surface, it is possible to reduce the drag/water resistance as the wearer moves through water because the water is able to flow smoothly over the upper peripheral wall.

Preferably, the outer surface defined by both the upper and lower peripheral walls is convex. This helps further reduce the water resistance as the water will flow smoothly over the lower peripheral walls as the wearer moves through the water.

The inventors have found that this smooth flow of water over the goggles helps minimise the chance of goggle displacement as the wearer moves through the water. Goggles having a concave upper peripheral wall do not exhibit this effect as the water flows over the upper peripheral wall and away from the lens portion whereas a convex wall portion causes the water to flow over the lens portion and then around the lower peripheral wall thus providing a force pushing the goggles in towards the face. The inventors have found that this effect is sufficient to hold the goggles onto the wearers face without a head strap.

In preferred embodiments the outer surface defined by the or each respective peripheral wall forms a smooth transition with the outer surface defined by the respective lens portions i.e. the peripheral wall(s) join the lens portions (which may have a curved or planar outer surface) through a continuous/smooth curve and there are no sudden changes in angle between the peripheral wall(s) and the respective lens portions. Many known goggles have peripheral walls extending almost perpendicularly to the lens portions so that the joint between the peripheral walls and lens portions are not smooth/continuously curved; there is an abrupt, angular joint. This abrupt angular joint creates a position of potential turbulence as the water flows over the goggles during use.

Most preferably, the outer surface is a smooth curve. For example, if the lens portions have a curved outer surface, the outer surface of the goggles is a continuous curve. As discussed above, this smooth curve facilitates a smooth flow of water over the goggles in a manner that forces the goggles onto the wearer's face and helps prevent dislodgement of the goggles.

Preferably, in use, the upper peripheral edge contacts the wearer's brow extra-orbitally. Preferably, the lower peripheral edge contacts the wearer's cheekbone. By providing extra-orbital goggles (as opposed to intra-orbital goggles which contact the wearer inside the wearer's eye socket), it is possible to provide goggles which substantially fill in the wearer's eye socket which minimises recesses thus minimising areas of possible water turbulence. Accordingly, this helps reduce water resistance and the chance of goggle dislodgement.

In preferred embodiments, the maximum distance between the upper and lower peripheral edges is at least 55 mm and preferably around 60 mm. This is a significantly larger distance than for known goggles. By providing a greater distance between the peripheral edges, it is possible to provide a shallowly curved convex upper peripheral wall which helps to further reduce the prominence of the leading edge and thus helps further reduce turbulence and thus minimises water resistance and the chance of goggle dislodgement.

It is preferable that, in use, the upper peripheral wall forms a smooth transition with the wearer's brow i.e. in use, the wearer's brow and upper peripheral wall form a smooth/continuous curve. As discussed above, many known goggles have peripheral was extending almost perpendicularly to the lens portions. Since the lens portions are generally perpendicular to the wearer's face, this means that the peripheral walls generally abut the wearer's face at right angles (usually just below the wearer's brow i.e. intra-orbitally). This presents a very prominent leading edge which increases turbulence and increases the likelihood that the goggles are dislodged from the wearer's face. Accordingly by providing an upper peripheral edge which contacts the wearer's brow extra-orbitally and forms a smooth transition with the wearer's brow, it is possible to maximise the smooth flow of water over the upper peripheral wall as the goggles do not present such a prominent leading edge.

Furthermore, it is preferable that, in use, the lower peripheral wall forms a smooth transition with the wearer's cheek bone i.e. in use, the wearer's cheek and lower peripheral wall form a smooth/continuous curve. As discussed above, many known goggles have peripheral walls which abut the wearer's face intra-orbitally at right angles. This presents a very recessed trailing edge which increases turbulence and drag. Accordingly by providing a lower peripheral edge which contacts the wearer's cheek extra-orbitally and forms a smooth transition with the wearer's cheek, it is possible to maximise the smooth flow of water over the lower peripheral wall.

In a second aspect, the present invention provides goggles having an outer surface defined by a pair of lens portions each having an upper peripheral wall extending to an upper peripheral edge which, in use contacts the wearer's brow extra-orb tally and a lower peripheral wall extending to a lower peripheral edge which, in use, contacts the wearer's cheek bone.

By providing extra-orbital goggles (as opposed to intra-orbital goggles which contact the wearer inside the wearer's eye socket), it is possible to provide goggles which substantially fill in the wearer's eye socket which minimises recesses thus minimising areas of possible water turbulence. Accordingly, this helps reduce water resistance and the chance of dislodgement by creating a smooth flow of water over the goggles.

Typically, the maximum distance between the upper and lower peripheral edges is at least 55 mm and preferably around 60 mm. This is a significantly larger distance than for known goggles. By providing a greater distance between the peripheral edges, it is possible to fill in the wearer's eye socket and streamline the wearer's head. This helps to further reduce the prominence of the leading edge and thus helps further reduce turbulence and thus minimises water resistance and the chance of dislodgement.

Preferably, said outer surface is a smooth curve i.e. the peripheral walls form a smooth transition with the respective lens portions i.e. the peripheral walls join the lens portions (which may have a curved or planar outer surface) through a continuous/smooth curve and/or there are no sudden changes in angle between the peripheral walls and the respective lens portions. Many known goggles have peripheral walls extending almost perpendicularly to the lens portions so that the joins between the peripheral walls and lens portions are not smooth/continuously curved; there is an abrupt, angular join. This abrupt angular join creates a position of potential turbulence as the water flows over the goggles during use.

Preferably, the outer surface defined by the upper peripheral walls is convex and most preferably, the outer surface defined by both the upper and lower peripheral was is convex. The convex curving of the peripheral wall(s) facilitates smooth water flow as discussed above in relation to the first aspect.

Preferably, in use, the upper peripheral wall forms a smooth transition with the wearer's brow and/or the lower peripheral wall forms a smooth transition with the wearer's cheek. As discussed above in relation to the first aspect, by providing an upper peripheral edge which contacts the wearer's brow extra-orbitally and forms a smooth transition with the wearer's brow, it is possible to maximise the smooth flow of water over the upper peripheral wall as the goggles do not present such a prominent leading edge. Furthermore, by providing a lower peripheral edge which contacts the wearer's cheek extra-orbitally and forms a smooth transition with the wearer's cheek, it is possible to maximise the smooth flow of water over the lower peripheral wall.

In a third aspect, the present invention provides goggles having an outer surface defined by a pair of lens portions each having an upper and a lower peripheral wall extending to an upper and lower peripheral edge respectively wherein, in use, said peripheral edges are in contact with the wearer's face, and wherein, in use, the goggles fill the wearer's eye sockets to streamline the wearer's head.

Many known goggles do not fill in the wearer's eye sockets but, instead sit within the eye socket. This means that recesses (defined by the eye sockets) remain and these create turbulent flow which acts as a resistance to movement through the water and can dislodge the goggles or, at least, compromise the water-tightness of the goggles. By providing goggles which fill in the wearer's eye sockets, preferably by fitting the wearer's face extra-orbitally, it is possible to eliminate these recesses and thus reduce water turbulence. This allows for a smooth flow of water over the goggles.

In preferred embodiments, in use, the upper peripheral edge contacts the wearer's brow extra-orbitally and/or the lower peripheral edge contacts the wearer's cheekbone. By providing extra-orbital goggles (as opposed to intra-orbital goggles which contact the wearer inside the wearer's eye socket), it is possible to provide goggles which substantially fill in the wearer's eye socket which minimises recesses thus minimising areas of possible water turbulence. Accordingly, this helps reduce water resistance and the chance of dislodgement.

Typically, the maximum distance between the upper and lower peripheral edges is at least 55 mm and preferably around 60 mm. This is a significantly larger distance than for known goggles. By providing a greater distance between the peripheral edges, it is possible to fill in the wearer's eye socket and streamline the wearer's head. This helps to further reduce the prominence of the leading edge and thus helps further reduce turbulence and thus minimises water resistance and the chance of dislodgement.

Preferably, the outer surface defined by the upper peripheral walls is convex and most preferably, the outer surface defined by both the upper and lower peripheral walls is convex. The convex curving of the peripheral wall(s) facilitates smooth water flow as discussed above in relation to the first aspect.

Preferably, the outer surface defined by the or each respective peripheral wall forms a smooth transition with the outer surface defined by the respective lens portions i.e. the peripheral wall(s) join the lens portions (which may have a curved or planar outer surface) through a continuous/smooth curve and there are no sudden changes in angle between the peripheral wall(s) and the respective lens portions. As discussed above, many known goggles have peripheral wads extending almost perpendicularly to the lens portions so that the joins between the peripheral walls and lens portions are abrupt and angular. This abrupt angular join creates a position of potential turbulence as the water flows over the goggles during use.

Preferably, the outer surface is a smooth curve. For example, if the lens portions have a curved outer surface, the outer surface of the goggles is a continuous curve. This smooth curve facilitates a smooth flow of water over the goggles in a manner that helps prevent dislodgement of the goggles. Most preferably, the outer surface is a smooth, continuous, convex surface.

Most preferably, the upper peripheral wall forms a smooth transition with the wearer's brow and the lower peripheral wall forms a smooth transition with the wearer's cheek. Accordingly, as discussed above in relation to the first aspect, by providing an upper peripheral edge which contacts the wearer's brow extra-orbitally and forms a smooth transition with the wearer's brow, it is possible to maximise the smooth flow of water over the upper peripheral wall as the goggles do not present such a prominent leading edge. By providing a lower peripheral edge which contacts the wearer's cheek extra-orbitally and forms a smooth transition with the wearer's cheek (unlike known goggles where the peripheral wall contacts the wearer's face at substantially 90 degrees), it is possible to maximise the smooth flow of water over the lower peripheral wall.

In a fourth aspect, the present invention provides goggles having an outer surface defined by a pair of lens portions each having an upper and a lower peripheral wall extending to an upper and lower peripheral edge respectively wherein, in use, said peripheral edges are in contact with the wearer's face, wherein the maximum distance between the upper and lower peripheral edges is greater than 55 mm. Preferably, the maximum distance between the upper and lower peripheral edges is around 60 mm.

This (55 mm) is a significantly larger distance than for known goggles. By providing a greater distance between the peripheral edges, it is possible to fill in the wearer's eye socket and streamline the wearer's head. This helps to reduce the prominence of the leading edge presented by the upper peripheral wall and thus helps further reduce turbulence and thus minimises water resistance and the chance of dislodgement by providing a smooth flow of water over the goggles.

In preferred embodiments, in use, the upper peripheral edge contacts the wearer's brow extra-orbitally and/or the lower peripheral edge contacts the wearer's cheekbone. By providing extra-orbital goggles (as opposed to intra-orbital goggles which contact the wearer inside the wearer's eye socket), it is possible to provide goggles which substantially fill in the wearer's eye socket which minimises recesses thus minimising areas of possible water turbulence. Accordingly, this helps reduce water resistance and the chance of dislodgement.

Most preferably, the upper peripheral wall forms a smooth transition with the wearer's brow and the lower peripheral wall forms a smooth transition with the wearer's cheek. Accordingly, as discussed above in relation to the first aspect, by providing an upper peripheral edge which contacts the wearer's brow extra-orbitally and forms a smooth transition with the wearer's brow, it is possible to maximise the smooth flow of water over the upper peripheral wall as the goggles do not present such a prominent leading edge. By providing a lower peripheral edge which contacts the wearer's cheek extra-orbitally and forms a smooth transition with the wearer's cheek (unlike known goggles where the peripheral wall contacts the wearer's face at substantially 90 degrees), it is possible to maximise the smooth flow of water over the lower peripheral wall.

Preferably, the outer surface defined by the upper peripheral walls is convex and most preferably, the outer surface defined by both the upper and lower peripheral walls is convex. The convex curving of the peripheral wall(s) facilitates smooth water flow as discussed above in relation to the first aspect.

Preferably, the outer surface defined by the or each respective peripheral wall forms a smooth transition with the outer surface defined by the respective lens portions i.e. the peripheral wall(s) join the lens portions (which may have a curved or planar outer surface) through a continuous/smooth curve and there are no sudden changes in angle between the peripheral wall(s) and the respective lens portions. As discussed above, many known goggles have peripheral walls extending almost perpendicularly to the lens portions so that the joins between the peripheral walls and lens portions are abrupt and angular. This abrupt angular join creates a position of potential turbulence as the water flows over the goggles during use.

Preferably, the outer surface is a smooth curve. For example, if the lens portions have a curved outer surface, the outer surface of the goggles is a continuous curve. This smooth curve facilitates smooth flow of water over the goggles in a manner that forces the goggles onto the wearer's face and helps prevent dislodgement of the goggles. Most preferably, the outer surface is a smooth, continuous, convex curve.

In a fifth aspect, the present invention provides goggles having an outer surface defined by a pair of lens portions each having an upper and a lower peripheral wall extending to an upper and lower peripheral edge respectively wherein, in use, said peripheral edges are in contact with the wearer's face, wherein the outer surface is a smooth curve.

The outer surface (i.e. the surface which faces away from the wearer in use) formed by the upper and lower peripheral walls forms a smooth transition with the outer surface formed by the respective lens portions i.e. the peripheral walls join the lens portions (which may have a curved or planar outer surface) through a smooth curve and there are no sudden changes in angle between the peripheral walls and the respective lens portions. Many known goggles have peripheral walls extending almost perpendicularly to the lens portions so that the joins between the peripheral walls and lens portions are not smooth/continuously curved; there is an abrupt, angular join. This abrupt angular join creates a position of potential turbulence as the water flows over the goggles during use. The smoothly curved outer surface provided by the fifth aspect of the present invention facilitates a smooth flow of water over the goggles in a manner that forces the goggles onto the wearer's face and helps prevent dislodgement of the goggles. The smooth curve also helps provide streamlined goggles which minimise drag/water resistance.

Preferably the smooth curve is a continuous curve i.e. all of the lens portions, upper peripheral wall and lower peripheral wall are curved.

Preferably, the smooth curve is a convex curve. Many known goggles have a substantially planar peripheral wall and this, necessarily extends back from the lens portion at substantially 90 degrees to the lens portion. This presents a prominent leading edge which creates considerable water resistance. By providing a smoothly curved convex goggle outer surface, it is possible to reduce the drag/water resistance as the wearer moves through water because the water is able to flow smoothly over the upper peripheral wall.

Preferably, in use, the upper peripheral edge contacts the wearer's brow extra-orbitally. Preferably, the lower peripheral edge contacts the wearer's cheekbone. By providing extra-orbital goggles (as opposed to intra-orbital goggles which contact the wearer inside the wearer's eye socket), it is possible to provide goggles which substantially fill in the wearer's eye socket which minimises recesses thus minimising areas of possible water turbulence. Accordingly, this helps reduce water resistance and the chance of dislodgement.

In preferred embodiments, the maximum distance between the upper and lower peripheral edges is at least 55 mm and preferably around 60 mm. This is a significantly larger distance than for known goggles. By providing a greater distance between the peripheral edges, it is possible to provide a shallowly curved upper and lower peripheral walls which helps to further reduce the prominence of the leading edge and thus helps further reduce turbulence and thus minimises water resistance and the chance of dislodgement.

It is preferable that, in use, the upper peripheral wall forms a smooth transition with the wearer's brow i.e. in use, the wearer's brow and upper peripheral wall form a smooth/continuous curve. As discussed above, many known goggles have peripheral walls extending almost perpendicularly to the lens portions. Since the lens portions are generally perpendicular to the wearer's face, this means that the peripheral walls generally abut the wearer's face at right angles (usually just below the wearer's brow i.e. intra-orbitally). This presents a very prominent leading edge which increases turbulence and increases the likelihood that the goggles are dislodged from the wearer's face. Accordingly by providing an upper peripheral edge which contacts the wearer's brow extra-orbitally and forms a smooth transition with the wearer's brow, it is possible to maximise the smooth flow of water over the upper peripheral wall as the goggles do not present such a prominent leading edge.

Furthermore, it is preferable that, in use, the lower peripheral wall forms a smooth transition with the wearer's cheek bone i.e. in use, the wearer's cheek and lower peripheral wall form a smooth/continuous curve. As discussed above, many known goggles have peripheral walls which abut the wearer's face intra-orbitally at right angles. This presents a very recessed trailing edge which increases turbulence and drag. Accordingly by providing a lower peripheral edge which contacts the wearer's cheek extra-orbitally and forms a smooth transition with the wearer's cheek, it is possible to maximise the smooth flow of water over the lower peripheral wall.

Preferably, each lens portion of the goggles according to any one of the aspects previously described further comprises an inner peripheral wall which extends to a respective inner peripheral edge which, in use, forms a seal against the wearer's face. This water-tight seal prevents ingress of water into the goggles to avoid discomfort and vision impairment for the wearer. In this case, the upper and lower peripheral was need not form a seal with the wearer's face but may simply abut the wearer's face.

The inner peripheral wall preferably extends substantially perpendicularly back from the lens portion and thus forms a secure seal with the wearer's face. The strength of the seal is not compromised by water flow because the upper and lower outer peripheral walls protect the inner walls from turbulent water flow. Accordingly, a strong seal can be maintained and water ingress minimised.

In a sixth aspect, the present invention provides goggles having an outer surface defined by a pair of lens portions each having an upper and a lower peripheral wall, wherein each lens portion further comprises an inner peripheral wall which extends to a respective inner peripheral edge which, in use, forms a seal against the wearer's face, and wherein the outer surface (i.e. the surface which faces away from the wearer and which, in use, is in contact with water) defined by the upper peripheral walls is convex.

By providing an upper peripheral wall having a convex outer surface, it is possible to reduce the drag/water resistance as the wearer moves through water because the water is able to flow smoothly over the upper peripheral wall. The upper peripheral wall deflects water from the inner peripheral wall (which forms a seal with the wearer's face) so that the seal is not compromised. The inventors have found that this effect is sufficient to hold the goggles onto the wearer's face without a head strap.

Preferably, the outer surface defined by both the upper and lower peripheral walls is convex. This helps further reduce the water resistance as the water will flow smoothly over the lower peripheral walls as the wearer moves through the water.

In preferred embodiments, the outer surface defined by the or each respective peripheral wall forms a smooth transition with the outer surface defined by the respective lens portions i.e. the peripheral wall(s) join the lens portions (which may have a curved or planar outer surface) through a continuous/smooth curve and there are no sudden changes in angle between the peripheral wall(s) and the respective lens portions. Any abrupt angular joins can create a position of potential turbulence as the water flows over the goggles during use.

Most preferably, the outer surface is a smooth curve. For example, if the lens portions have a curved outer surface, the outer surface of the goggles is a continuous curve. As discussed above, this smooth curve facilitates a smooth flow of water over the goggles in a manner that helps prevent dislodgement of the goggles.

In a seventh aspect, the present invention provides goggles having an outer surface defined by a pair of lens portions each having an upper and a lower peripheral wall wherein each lens portion further comprises an inner peripheral wall which extends to a respective inner peripheral edge which, in use, forms a seal against the wearer's face, and wherein the outer surface is a smooth curve.

The outer surface (i.e. the surface which faces away from the wearer in use) formed by the upper and lower peripheral wads forms a smooth transition with the outer surface formed by the respective lens portions i.e. the peripheral walls join the lens portions (which may have a curved or planar outer surface) through a smooth curve and there are no sudden changes in angle between the peripheral walls and the respective lens portions. Any abrupt angular joins create a position of potential turbulence as the water flows over the goggles during use. The smoothly curved outer surface provided by the seventh aspect of the present invention facilitates a smooth flow of water over the goggles in a manner that helps prevent dislodgement of the goggles. The smooth curve also helps provide streamlined goggles which minimise drag/water resistance.

Preferably the smooth curve is a continuous curve i.e. all of the lens portions, upper peripheral wall and lower peripheral wall are curved.

Preferably, the smooth curve is a convex curve. By providing a smoothly curved convex goggle outer surface, it is possible to reduce the drag/water resistance as the wearer moves through water because the water is able to flow smoothly over the upper peripheral wall. The inventors have found that a head strap can be omitted from goggles if the outer surface of the goggles is a smooth convex curve.

Preferably, in all aspects, the upper and lower peripheral walls are formed of a rigid plastics material which does not significantly flex. This rigidity helps protect any inner peripheral wall from any water turbulence.

Preferably, in all aspects previously described, the respective upper and lower peripheral walls are joined to form a complete peripheral wall which completely surrounds its respective lens portion. Preferably, the entire outer surface of the continuous peripheral wall is convex. This helps further minimise water turbulence and hence minimise water resistance.

Preferably, in all aspects previously described, the goggles are such that, in use, the wearer's nostrils are uncovered (unlike in a diving mask).

Preferably, the lens portions in may of the aspects are joined to one another via a nose bridge. Most preferably, the lens portions are joined to one another via a rigid nose bridge e.g. a nose bridge formed of a rigid plastics material such as nylon, polypropylene or polycarbonate. Such a rigid nose bridge helps maintain the seal between the goggles and the wearer's face because the goggles do not flex.

In alternative embodiments, the lens portions may be directly joined to one another such that they form a singe, elongated lens such as those provided in diving masks.

The features of any of the aspects described above can be combined with any of the features of one or more of the other aspects.

DETAILED DESCRIPTION OF THE INVENTION

FIGS. 1 to 4 show swimming goggles 1 according a first embodiment of the present invention.

The swimming goggles 1 comprises a pair of lens portions 2 (preferably formed of polycarbonate) joined by a nose bridge 3 (preferably formed of thermoplastic rubber (TPR)).

Figure 1:
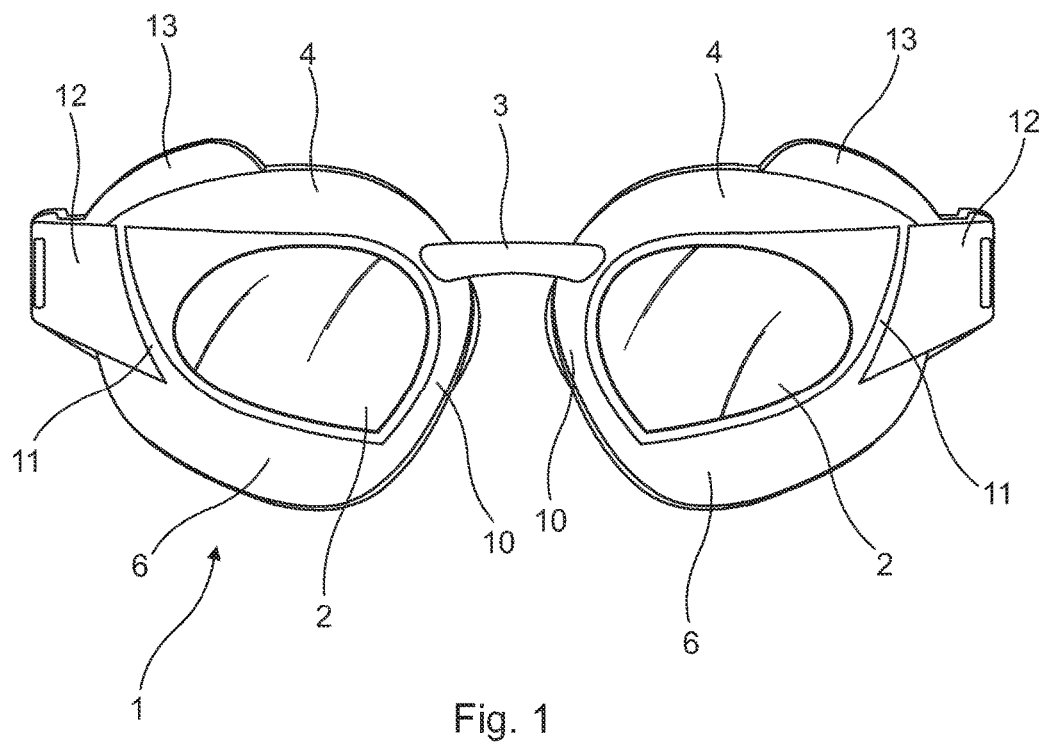
FIG. 1 shows a front view of swimming goggles forming a first embodiment of the present invention.
Figure 2:
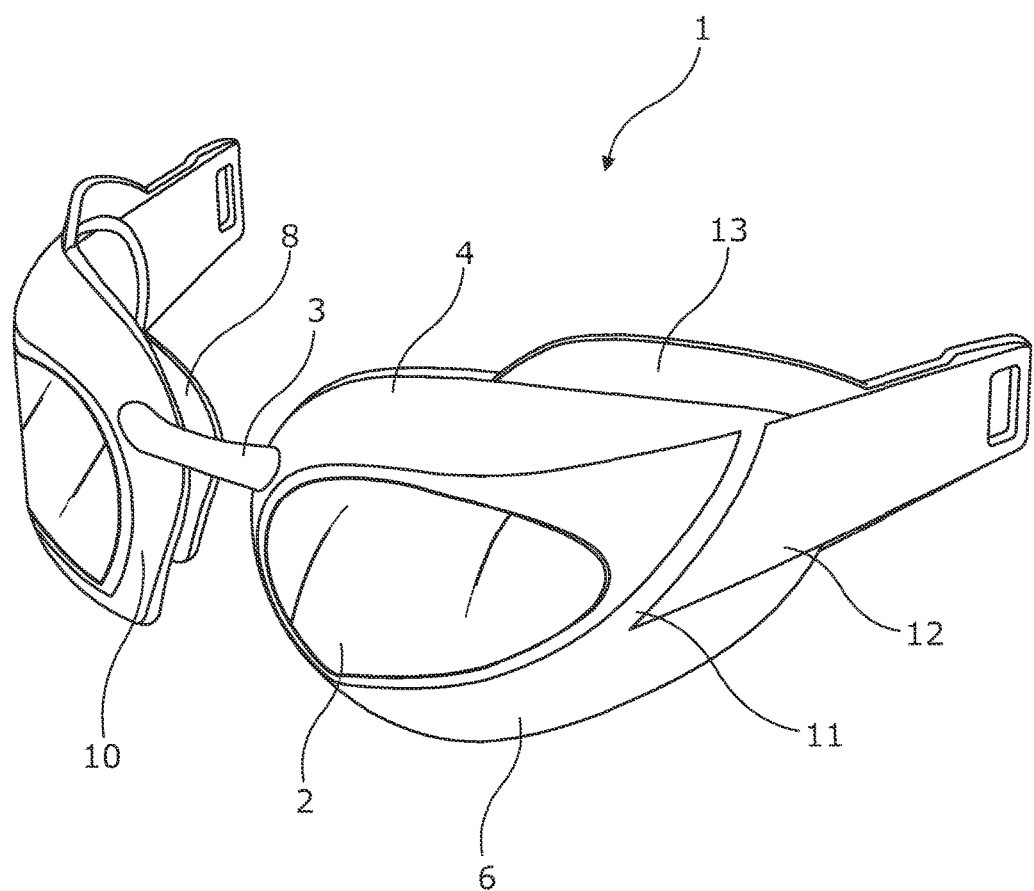
FIG. 2 shows a front perspective view of swimming goggles forming a first embodiment of the present invention.
Figure 3:
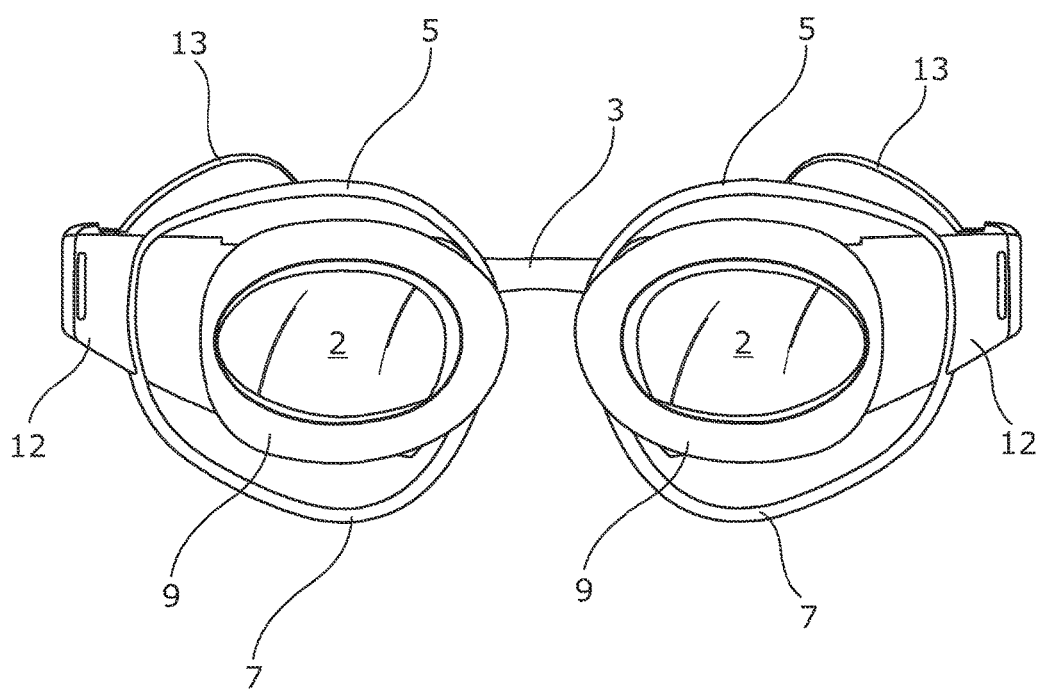
FIG. 3 shows a rear view of swimming goggles forming a first embodiment of the present invention.

Each lens portion has an upper peripheral wall 4 extending to an upper peripheral edge 5 (shown in FIG. 3) and a lower peripheral wall 6 extending to a lower peripheral edge 7 (shown in FIG. 3). The peripheral walls are preferably formed of polycarbonate.

The upper and lower peripheral was 4, 6 are continuous and completely surround the respective lens portion 2. The upper and lower peripheral was 4, 6 meet at an inside portion 10 adjacent the wearer's nose and at an outside portion 11 adjacent the wearer's respective ear. The outside portion is provided with an extension 12 for connection to a head strap (not shown).

The lens portions 2 and peripheral walls 4, 6 define the outer surface of the goggles i.e. the surface which faces away from the wearer and which is in contact with the water during use.

Figure 4:
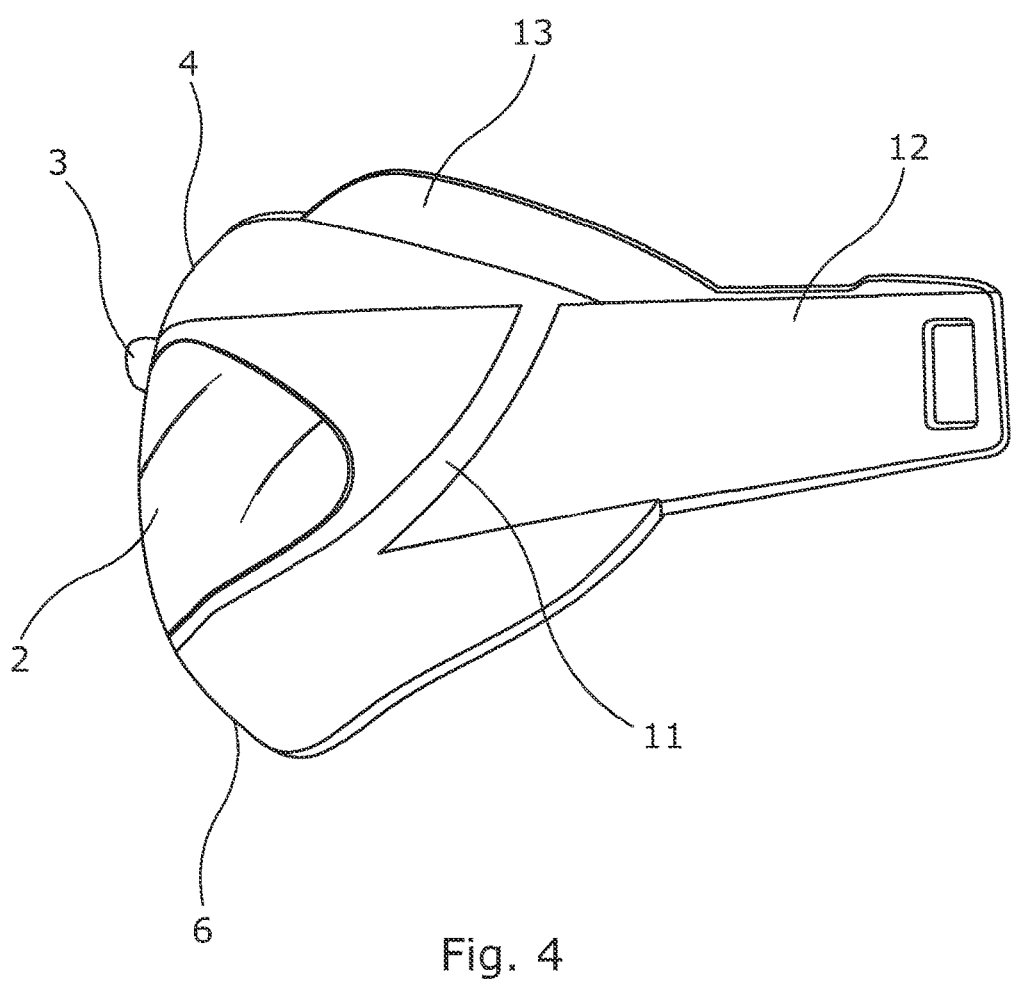
FIG. 4 shows a side view of swimming goggles forming a first embodiment of the present invention.

As can be clearly seen in FIG. 4, the upper peripheral wall 4 is convex. By providing an upper peripheral wall having a convex outer surface, it is possible to reduce the drag/water resistance as the wearer moves through water because the water is able to flow smoothly over the upper peripheral wall (which will form the leading edge as the swimmer moves through the water).

FIG. 4 also shows that the lower peripheral wall 6 is convex. This helps further reduce the water resistance as the water will flow smoothly over the lower peripheral wall as the wearer moves through the water.

The outer surface defined by the peripheral walls 4, 6 forms a smooth transition with the outer surface defined by the respective lens portions 2 i.e. the convex peripheral was 4, 6 join the lens portions 2 (which are curved in this embodiment) through a continuous/smooth curve. There are no sudden changes in angle between the convex peripheral was 4, 6 and the respective lens portions 2.

It can be clearly seen in FIG. 4 that the outer surface of the goggles 1 is a smooth, continuous convex surface. As discussed above, this smooth curve facilitates a smooth flow of water over the goggles in a manner that helps prevent dislodgement of the goggles.

Figure 5:
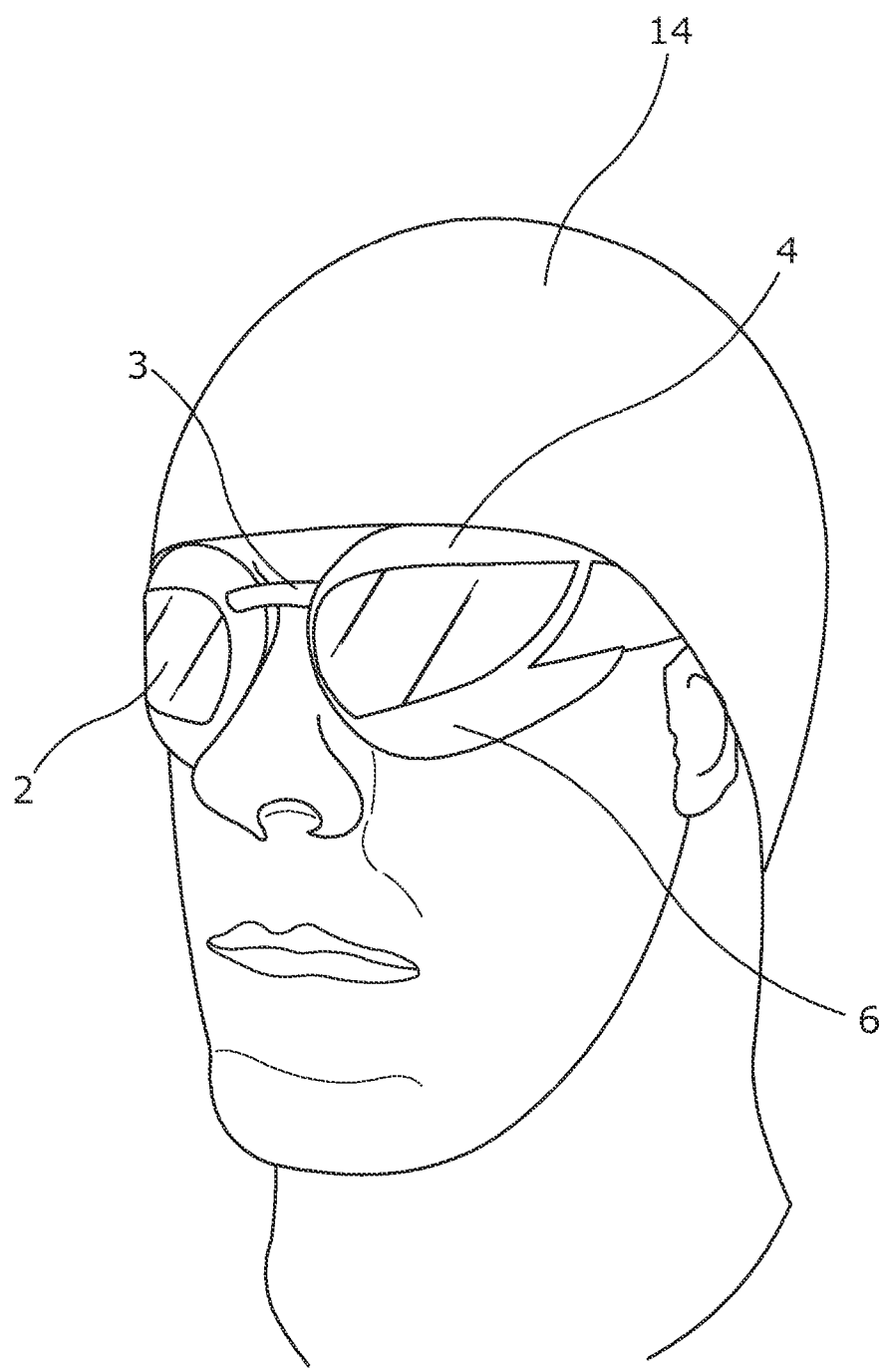
FIG. 5 shows the swimming goggles of the first embodiment when worn.

In use, the upper peripheral edge 5 contacts the wearer's brow extra-orbitally and the lower peripheral edge 7 contacts the wearer's cheekbone as shown in FIG. 5. By providing extra-orbital goggles (as opposed to intra-orbital goggles which contact the wearer inside the wearer's eye socket), it is possible to provide goggles which substantially fill in the wearer's eye socket which minimises recesses thus minimising areas of possible water turbulence. Accordingly, this helps reduce water resistance and the chance of goggle dislodgement (even in the absence of a head strap).

The upper peripheral wall 4 forms a smooth transition with the wearer's brow i.e. the wearer's brow and upper peripheral wall 4 form a smooth/continuous curve. This makes it possible to maximise the smooth flow of water over the upper peripheral wall as the goggles do not present a prominent leading edge.

The lower peripheral wall 6 forms a smooth transition with the wearer's cheek bone i.e. in use, the wearer's cheek and lower peripheral wall form a smooth/continuous curve. This makes it possible to maximise the smooth flow of water over the lower peripheral wall.

The maximum distance between the upper and lower peripheral edges 5, around 60 mm. This is a significantly larger distance than for known goggles. By providing a greater distance between the peripheral edges 5, 7, it is possible to provide shallowly curved upper and lower peripheral walls 4, 6 which helps to further reduce the prominence of the leading edge and thus helps further reduce turbulence and thus minimises water resistance and the chance of dislodgement.

Each upper peripheral edge 5 has an upwardly extending tab 13 which, in use, is overlaid by a forward edge of a swimming cap 14 as shown in FIG. 5. The upwardly extending tabs 13 are formed at the outer side of the upper peripheral edge 5 (i.e. on the area which, in use, is proximal the wearer's ears) but they could alternatively be provided on the inner side (i.e. the area which, in use, is proximal the wearer's nose). The upwardly extending tabs 13 extend such that, in use, they rest against the wearer's brows i.e. the term "upwards" is used to designate a direction which, in use, extends from the peripheral edge over the wearer's brows.

These tabs 13 are provided such that, in use, they may be overlaid (preferably completely overlaid) by the forward edge of a swimming cap 14. This helps secure the goggles against the wearer's face so that forces generated, for example, upon diving into the ater, do not dislodge the goggles.

Figure 6:
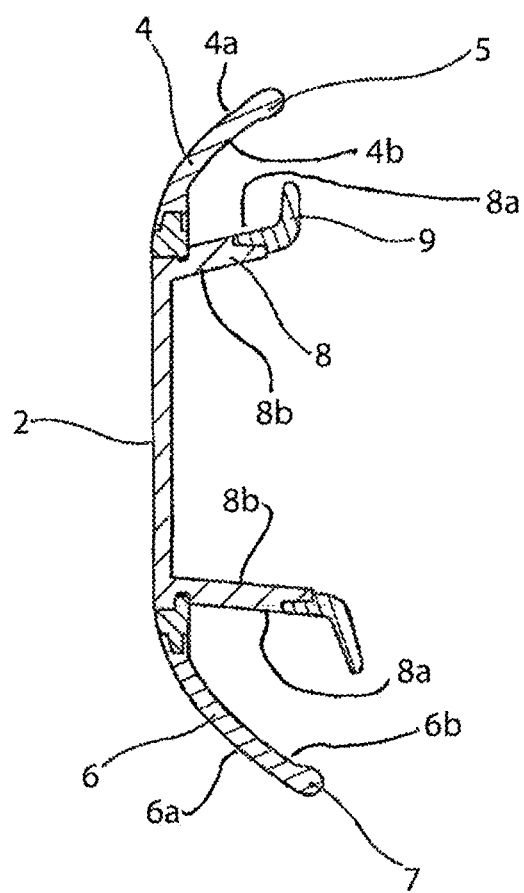
FIG. 6 shows a cross section through the lens portion and upper and lower peripheral walls for a second embodiment of the present invention.
Figure 7:
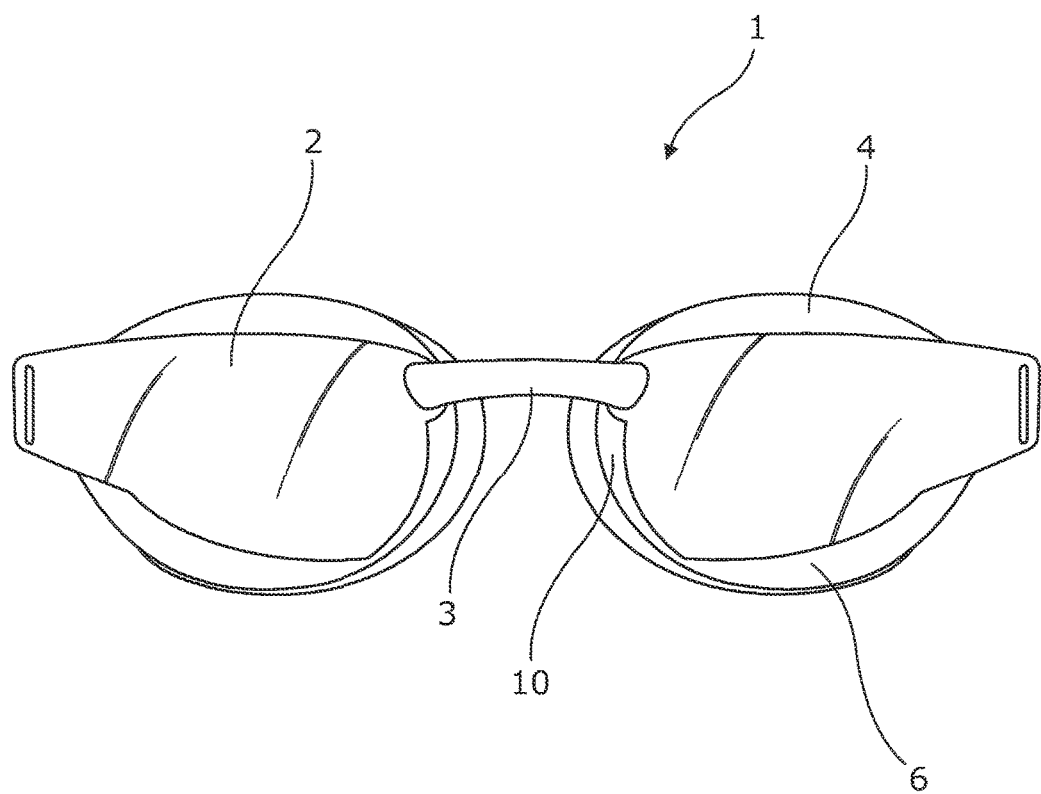
FIG. 7 shows a front view of swimming goggles forming a third embodiment of the present invention.
Figure 8:
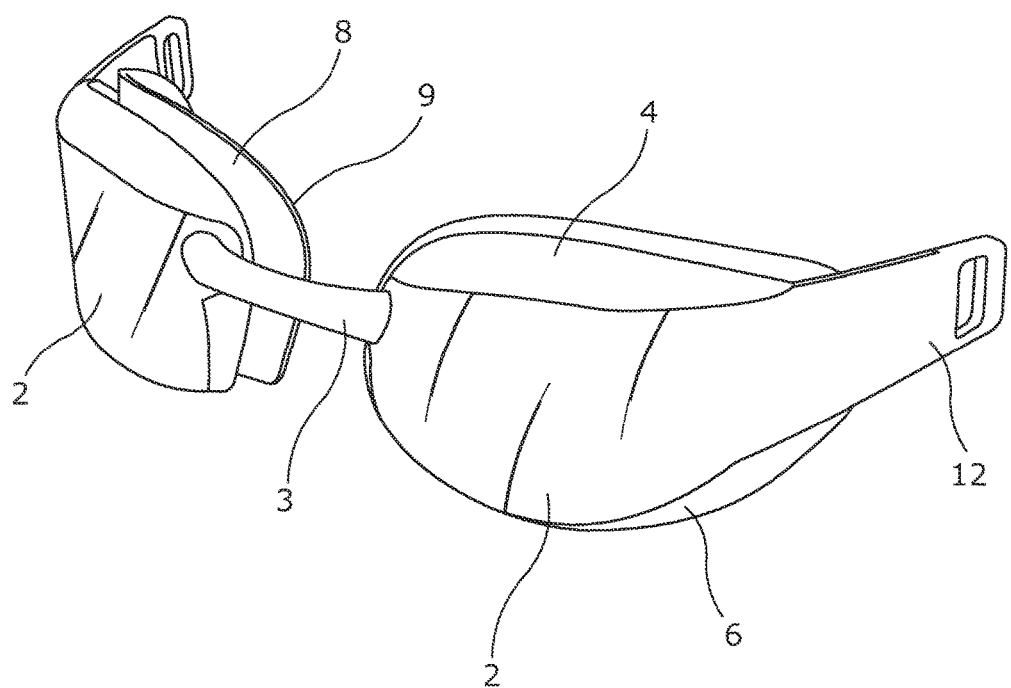
FIG. 8 shows a front perspective view of swimming goggles forming a third embodiment of the present invention.
Figure 9:
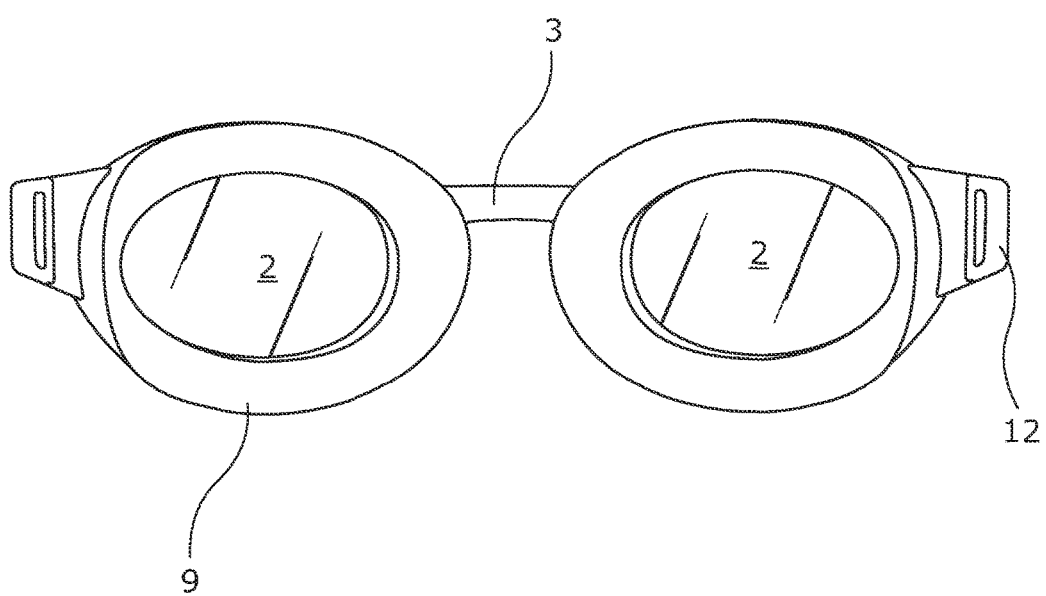
FIG. 9 shows a rear view of swimming goggles forming a third embodiment of the present invention.

The upper peripheral wall 4 and lower peripheral wall 6 are formed of rigid plastic material (e.g. polycarbonate) and, in use, sit in abutment with the wearers face rather than forming a water tight seal. The peripheral walls 4 and 6 have outer surfaces 4a and 6a, respectively, and inner surfaces 4b and 6b, respectively. The water tight seal around each eye is formed by an inner peripheral wall 8 which extends substantially perpendicularly from the lens portion and terminates in an inner peripheral edge 9. The inner peripheral wall 8 has an outer surface 8a and an inner surface 8b. This is most clearly seen in FIG. 6 which is a cross section through a lens portion 2 and associated peripheral walls 4, 6 for second embodiment which differs from the first embodiment in that the outer surface defined by the lens portion 2 is planar. However, it can be seen that the outer surface of the goggles of the second embodiment still forms a smooth convex curve (with zero curvature at the lens portions). There are no abrupt transitions between the lens portion 2 and the peripheral walls 4, 6.

FIGS. 7 to 10 show swimming goggles 1 according a third embodiment of the present invention.

The swimming goggles 1 comprises a pair of lens portions 2 (preferably formed of polycarbonate) joined by a nose bridge 3 (preferably formed of a rigid plastics material such as nylon).

Each lens portion has an upper peripheral wall 4 and a lower peripheral wall 6. The peripheral walls are preferably formed of polycarbonate.

The upper and lower peripheral walls 4, 6 meet at an inside portion 10 adjacent the wearer's nose. The lens portion is provided with an extension 12 for connection to a head strap (not shown).

A water tight seal around each eye is formed by an inner peripheral wall 8 which extends substantially perpendicularly from the lens portion and terminates in an inner peripheral edge 9. This is most clearly seen in FIG. 8. In this embodiment, the outer surface defined by the lens portion 2 is a convex curve. In other embodiments (not shown), the outer surface formed by the lens portions may be planar although still forming a smooth convex curve (with zero curvature at the lens portions). There are no abrupt transitions between the lens portion 2 and the peripheral walls 4, 6.

The lens portions 2 and peripheral walls 4, 6 define the outer surface of the goggles i.e. the surface which faces away from the wearer and which is in contact with the water during use.

Figure 10:
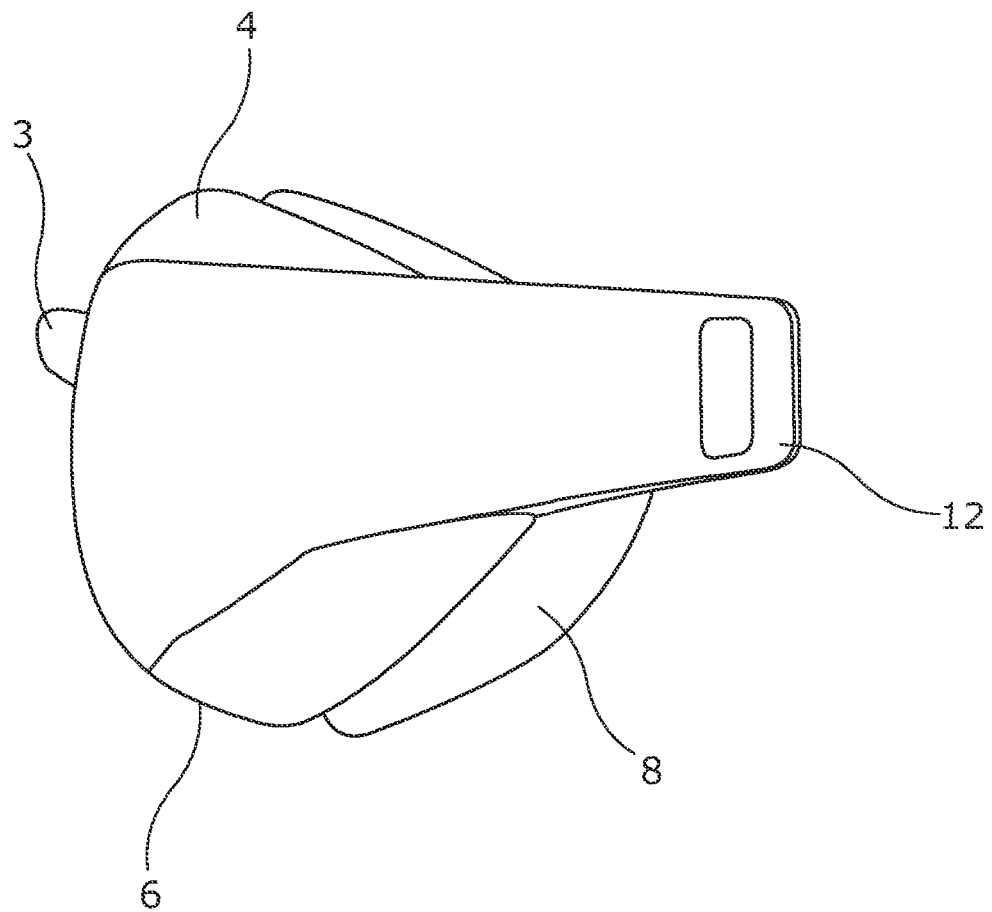
FIG. 10 shows a side view of swimming goggles forming a third embodiment of the present invention.

As can be clearly seen in FIG. 10, the upper peripheral wall 4 is convex. By providing an upper peripheral wall having a convex outer surface, it is possible to reduce the drag/water resistance as the wearer moves through water because the water able to flow smoothly over the upper peripheral wall (which will form the leading edge as the swimmer moves through the water).

The outer surface deflects water away from the inner peripheral wall such that the water tight seal remains uncompromised. The inventors have found that this deflection is sufficient to enable the goggles to be worn without any head strap.

FIG. 10 also shows that the lower peripheral wall 6 is convex. This helps further reduce the water resistance as the water will flow smoothly over the lower peripheral wall as the wearer moves through the water.

The outer surface defined by the peripheral walls 4, 6 forms a smooth transition with the outer surface defined by the respective lens portions 2 i.e. the convex peripheral walls 4, 6 join the lens portions 2 (which are curved in this embodiment) through a continuous/smooth curve. There are no sudden changes in angle between the convex peripheral walls 4, 6 and the respective lens portions 2.

It can be clearly seen in FIG. 10 that the outer surface of the goggles 1 is a smooth, continuous convex surface. As discussed above, this smooth curve facilitates a smooth flow of water over the goggles in a manner that forces the goggles onto the wearer's face and helps prevent dislodgement of the goggles (even in the absence of a head strap).

The skilled person will appreciate that the goggles illustrated in the Figures and described above are examples embodying inventive concepts described herein and that many and various modifications can be made without departing from the invention.

The invention claimed is:

1. Goggles having an outer surface defined by a pair of eye pieces, each having a lens portion and each having an upper and a lower peripheral wall extending from the lens portion to an upper and a lower peripheral edge, respectively, each of the upper and lower peripheral walls having an outer surface and an inner surface, wherein, in use, said peripheral edges are configured to be in contact with the wearer's face, each eye piece further comprising an inner peripheral wall extending substantially perpendicularly inwardly from its respective lens portion and terminating at an inner peripheral edge which is configured to form a seal against the wearer's face, each inner peripheral wall having an outer surface and an inner surface, and wherein a space is formed between the outer surface of each inner peripheral wall and the inner surfaces of each of the upper and lower peripheral walls, and wherein the outer surfaces of each of the upper and lower peripheral walls are convex and the outer surface of each eye piece from the upper peripheral edge to the lower peripheral edge through the upper peripheral wall, the lens portion and the lower peripheral wall, is a smooth continuous curve.

2. Goggles according to claim 1 wherein, in use, the upper peripheral edge is configured to engage wearer's face outside of the eye socket.

3. Goggles according to claim 2 wherein, in use, the upper peripheral wall is configured to form a smooth transition with the wearer's brow.

4. Goggles according to claim 1 wherein, in use, the lower peripheral edge is configured to contact the wearer's cheekbone.

5. Goggles according to claim 4 wherein, in use, the lower peripheral wall is configured to form a smooth transition with the wearer's cheek.

6. Goggles according to claim 1 wherein, in use, the goggles are configured to surround the wearer's eye sockets to streamline the wearer's head.

7. Goggles according to claim 1 wherein the maximum distance between the upper and lower peripheral edges is greater than 55 mm.

8. Goggles according to claim 1 wherein, in use, the goggles are configured to leave the wearer's nostrils uncovered.

9. Goggles according to claim 1 wherein the lens portions are joined to one another through a nose bridge.

* * * * *